United States Patent [19]

Kuettner

[11] 4,356,261
[45] Oct. 26, 1982

[54] ANTI-INVASION FACTOR CONTAINING CULTURES

[75] Inventor: Klaus E. Kuettner, Chicago, Ill.

[73] Assignee: Rush-Presbyterian-St. Luke's Medical Center, Chicago, Ill.

[21] Appl. No.: 142,731

[22] Filed: Apr. 22, 1980

[51] Int. Cl.$^3$ .......................... C12N 5/00; C12P 21/00
[52] U.S. Cl. .................................... 435/68; 435/240; 424/95
[58] Field of Search ................... 435/68, 240; 424/95, 424/177

[56] References Cited

U.S. PATENT DOCUMENTS

| Re. 30,239 | 3/1980 | Kuettner et al. | 424/95 |
| 3,450,598 | 6/1969 | Welsh et al. | 435/240 |
| 4,176,177 | 11/1979 | Kuettner | 424/95 |

OTHER PUBLICATIONS

Müller et al., *Exp. Cell Res.*, 108, 47–55, (1977).
Klagsbrun, *Methods in Enzymology*, LVIII, Academic Press, New York, 560–564, (1979).
O. W. Wiebkin and H. Muir, FEBS Letters, vol. 37, No. 1, (1973), pp. 42–46.

*Primary Examiner*—Esther M. Kepplinger
*Attorney, Agent, or Firm*—Fitch, Even, Tabin, Flannery & Welsh

[57]  ABSTRACT

Chondrocytes are cultured to produce cartilage tissue from which an anti-invasion factor (AIF) may be recovered. Mammalian cartilage providing at least about 60% viable chondrocytes is enzymatically digested to denude the cells of their extracellular matrix. The denuded cells are plated at high density and cultured to produce cartilage tissue.

4 Claims, No Drawings

ANTI-INVASION FACTOR CONTAINING CULTURES

The invention described herein was made in the course of work under a grant or award from the Department of Health, Education and Welfare.

The present invention relates to culturing of cartilage cells in vitro to produce cartilage tissue. The resultant tissue and its growth medium has utility as a source of a protein fraction having anti-invasive properties.

Certain tissues have a high resistance to invasion by foreign cells, and cartilage tissue has been found to have especially high resistance to invasion by foreign cells such as cancer cells and blood capilliary cells.

Described in my U.S. Pat. No. 4,042,457, issued Aug. 16, 1977, is a protein fraction obtained from cartilage tissues which inhibits cell proliferation and tissue invasion. This protein fraction was also found to have inhibitory effects on bone resporption as described in my U.S. Pat. No. 4,176,177, issued Nov. 27, 1979. This protein fraction will hereinafter be referred to as anti-invasion factor, or AIF.

AIF has been shown to express anti-tumor properties both in vivo and in vitro. Tumors grown in vivo shrink in the presence of AIF. Tumorous mice injected with sufficient AIF demonstrate regression of the tumors and a lack of new daughter tumors. Accordingly, AIF holds promise as a cancer-treating agent. However, AIF must be made more readily obtainable for its full drug potential to be realized.

Current methods of obtaining AIF involve obtaining waste animal parts from slaughterhouses, separating the cartilage tissue and extracting the AIF. This is a long and tedious procedure. Cartilage tissue is a part of the skeleton of animals and, accordingly, bones and adjacent muscles and other connective tissues must be separated to reach the cartilage to remove the small amount of cartilage tissue therefrom.

As a first step toward increasing the available amount of AIF, it would be desirable to obtain cartilage tissue by means other than separating animal joints, such as by culturing the cartilage cell population, chondroblasts, or chondrocytes to obtain cartilage tissue having significant amounts of AIF.

Culturing of cartilage cells containing significant amounts of AIF is complicated by the inherent nature of cartilage tissue. Cartilage cells in vivo produce an extracellular matrix which separates one cell from another. One of the main functions of the cells comprising cartilage would appear to be the production of the extracellular matrix. These cartilage-forming cells are called chondroblasts. While an animal is growing, the cartilage is growing and many cartilage cells retain their ability to reproduce.

In an adult animal, the majority of cartilage cells are embedded within the extracellular matrix and are nonreproductive and responsible for the maintenance of the tissue integrity. Even though functionally incorrect, all cartilage cells, whether reproductively active or inactive, are generally called chondrocytes. The extracellular matrix, comprised largely of collagen type II and proteoglycans is extremely long lasting; cartilage collagen in certain animals may have a half-life of several years. Accordingly, when the chondrocytes have produced the extracellular matrix around themselves and thereby produced the cartilage tissue, they have generally served their function. Chondrocytes from adult cartilage tissue have generally lost their in vivo potential to reproduce.

The most actively reproducing chondrocytes are those found in embryonic tissue. However, embryonic tissue appears to contain less anti-invasion factor than adolescent tissue. Illustrative of this fact is that while adult cartilage tissue is nonvascular, as a result of the anti-invasion factor preventing the ingrowth of capillary cells, some early embryonic cartilage is supplied by the vascular system.

A further well recognized difficulty in culturing cartilage tissue is the fact that chondrocytes do not necessarily produce cartilage tissue when cultured.

When chondrocytes obtained from most cartilage tissue are cultured, the resulting tissue includes fibroblasts, that is, cells which have not differentiated into cartilage producing cells or modulated chondrocytes with fibroblastic gene expression. Such cultures produce collagen type I, the most common type of collagen which is found in tissues such as skin, bone, muscle, etc., as well as collagen type II, the type of collagen found in cartilage. In order to produce true cartilage tissue, therefore, it is necessary that the chondrocytes maintain their differentiated state and proliferate only into cartilage type cells with an extracellular matrix therearound containing only collagen type II. While collagen type II would appear not to be a component of AIF, the production of collagen type II is a good indicator of the presence of AIF as both collagen type II and AIF are closely associated with cartilage tissue.

It has been recognized that the relative amounts of collagen type I and collagen type II which are obtained from chondrocyte cultures depend on the environment surrounding the cultured chondrocytes. Different cellular environments give rise to cultures with collagen type I and collagen type II in varying amounts. An extremely significant environmental factor has been shown to be the density in which the chondrocytes are suspended and plated. For uncertain reasons, chondrocytes resist contact with other chondrocytes, and when chondrocytes are in contact with other such cells, they produce around themselves the extracellular matrix found in cartilage. Studies with embryonic chicken chondrocytes have shown that when the chondrocytes are plated in very high density, primarily collagen type II is produced. Likewise, it has been found in fetal bovine cartilage tissue that a high density of plated chondrocytes yields a high percentage of collagen type II as compared to collagen type I.

The plating of mature mammalian chondrocytes to produce cartilage tissue heretofore has been less than completely successful in that culturing of mammalian tissue has generally produced cultures having a mixture of collagen type I and collagen type II.

In order that anti-invasion factor may be produced in greater amounts, it would be desirable to be able to culture mammalian chondrocytes to produce cartilage tissue. To insure sufficient yield of anti-invasion factor, it would be highly desirable to culture chondrocytes to produce cultures with extracellular matrices containing only collagen type II.

Accordingly, it is an object of the present invention to culture mammalian chondrocytes to produce cartilage tissue with high amounts of anti-invasion factor.

The objects are achieved in the present invention by plating, in high density, chondrocytes obtained from mammals which have a high percentage of viability so that, generally, each active chondrocyte is in surface contact with another active chondrocyte. While it has been recognized that high density plating tends to produce cartilage tissue, previous attempts have been less than successful due to the failure to concentrate reproductively viable cells in sufficient density.

To more fully understand the present invention, the culturing of chondrocytes to produce cartilage tissue will now be described in greater detail.

As hereinabove described, the most active cartilage tissue, i.e. embryonic tissue, is limited in the production of anti-invasion factor, and mature cartilage is metabolically slow and contains cells which are generally inactive, and therefore, when mature tissue is degraded by the best known methods a very low yield of viable chondrocytes is provided. It is therefore desirable to obtain cells from non-embryonic animals which nevertheless provide a high percentage of viable chondrocytes.

It has been found that the chondrocytes of weight-bearing articular cartilage, as are found in the ankles and toes of adolescent mammals, have a very high viability and high degree of biological activity. In particular, calf fetlock cartilage contain a high percentage of reproductively and metabolically active chondrocytes. A growing calf gains weight very rapidly, and to maintain the calf's weight, the weight bearing limbs, such as the hooves and fetlocks, enlarge proportionally, and the cartilage tissue proportionally grows and expands.

Calf fetlocks are generally a waste product of slaughterhouses and may therefore be obtained with relative ease. After the animal is slaughtered, the fetlocks are transported to the laboratory. The skin is removed, the first phalangal joint is carefully opened under aseptic conditions and the synovial fluid is removed. The cartilage of the exposed joint is carefully shaved off so as to obtain as much cartilage tissue as possible and yet avoid contamination by other tissues such as bone. The shavings are collected in Ham's F-12 medium or any ther tissue culture medium suitable for tissue survival but enriched in antibiotics and antifungal agents, e.g. 50 micrograms gentamycin and 5 micrograms of beta-amphotericin per milliliter.

The cartilage shavings contain both the chondrocytes and the extracellular matrix. In order that the cells may be cultured, the extracellular matrix must be removed. This is done enzymatically by various enzymes which digest the proteins of the extracellular matrix. The shavings are first digested with pronase in an amount between about 0.5 and about 2.0% and most preferably about 1% weight per volume in Ham's F-12 medium or other suitable tissue culture medium containing 5% bovine serum for 90 minutes. The pronase will digest most of the proteins of the extracellular matrix including proteoglycans and some collagen. The shavings after washing and centrifugation are further digested in medium containing 5% bovine serum and between about 0.1 and about 1% weight per voluem collagenase for a period of about 1-2 hours to digest the remaining collagen from around the cells. The cells, after washing and centrifugation, are further digested with between about 0.1% and about 3% weight per volume trypsin or testicular hyaluronidase and most preferably about 0.25% trypsin or hyaluronidase for between about 5 and about 10 minutes in the presence of 5% bovine serum. The trypsin digests any remaining extracellular proteins and testicular hyaluronidase digests the sugar moieties attached to any remaining extracellular protein, thereby denuding the chondrocytes.

Digestion of the extracellular material by the proteolytic enzymes is very harsh to the cells. The enzymes, in addition to attacking the matrix, begin to attack the cell membranes. Accordingly, the cells are left in a weakened state after digestion. Mammalian serum, preferably fetal serum, is therefore added to the digestive mixture so that the denuded cells may be coated and protected with serum immediately after being denuded.

The fact that serum and digestive enzymes can be used simultaneously is somewhat surprising for several reasons. It would be expected that all the trypsin would attack the serum and would bind, for the most part, with proteins of the serum. Furthermore, serum contains trypsin inhibitors which should affect trypsin's action vis-a-vis the extracellular matrix. Nevertheless, it has been found that this combination of trypsin along with serum produces chondrocytes with a high percentage of viability.

The isolated cells are collected by centrifugation at about 900 rpm for 10 minutes. The cell pellet is washed in phosphate buffered physiological saline pH 7.4 as described in *J. Cell Biol.* 49: 451(1971), and the cells are suspended in Ham's F-12 medium without serum. The cells are then passed through a 90 micrometer Nitex screen to separate the cells which are resuspended in Ham's F-12 medium containing about 5-10 percent serum. Sufficient cells are added to the medium to achieve a concentration of at least $10^6$ cells per milliliter.

Cells may be grown in culture dishes such as 35 mm tissue culture dishes and for morphological observation may be grown on $26 \times 34$ mm cover slips submerged in culture dishes.

In order to produce cartilage tissue, at least a monolayer of denuded chondrocytes must be originally plated. Most of these cells must be reproductively viable in order for growing chondrocytes to contact other growing chondrocytes to produce the extracellular matrix. Accordingly, cartilage tissue, which will provide at least about 60% viable chondrocytes, is selected for culturing. Herein, the percent of viable chondrocytes referred to is that percent of chondrocytes which is provided by careful but thorough degradation of the extracellular matrix of a particular tissue.

It has been found that chondrocytes obtained from fetlock cartilage of adolescent bovines may be 89% reproductively viable. This is somewhat surprising in light of the viability of chondrocytes obtained from other tissue, such as nasal cartilage, from which, because of its easy accessibility, cartilage tissue is commonly obtained. For example, from the same animal 89% reproductively viable chondrocytes may be obtained from fetlock cartilage degradation while only 10 to 15 percent reproductively viable chondrocytes may be obtained from nasal cartilage degradation. It is therefore possible to obtain and plate reproductively viable fetlock-derived chondrocytes in sufficiently high density to produce at least a monolayer of viable cells, such a density being necessary to produce cartilage tissue.

While chondrocytes grown in culture dishes produce the desired tissue, significant amounts of tissue cannot thereby be produced. Culture dishes are small. Furthermore, an important factor in achieving good yields of cartilage tissue is the atmosphere in which the chondrocytes grow. After layers of cells begin to accumulate, the lower layers are shielded from the atmosphere. Inability to maintain optimal gas balance for the shielded layers results in reduced production of cultured material.

In order to produce cultured material in large quantities, it is desirable to use roller bottles. The application of culturing techniques to roller bottle technology is necessary if a culture is to be mass produced. Roller bottles have large surface areas and permit easy exchange of the medium and gases. Because of the sensitivity and difficulty of culturing chondrocytes, roller bottle technology was heretofore considered unsuitable for the culturing of cartilage tissue. However, it has been found that good growth of cartilage tissue may be achieved in roller bottles from cells denuded according to the above methods.

The cultures are maintained in Ham's F-12 medium supplemented with the antibiotic and antifungal agents described above as well as with 50 micrograms of ascorbic acid per ml. and 15% bovine serum. The cells are cultured at 37° in a humidified atmosphere containing at least 5% carbon dioxide. The medium is changed every other day. After about 10 days, nodules appear which contain extensive extracellular matrix chemically identified as being cartilaginous in nature.

AIF may be extracted from the chondrocyte cultures as well as the collected growth media according to the methods described in my U.S. Pat. No. 4,042,457.

EXAMPLE 1

About $10^8$ chondrocytes are prepared and cultured by the above described method in a roller bottle having 500 cm² of interior surface to achieve a plated density of about $2 \times 10^5$ cells per cm² of interior surface area. After 16 days, the culture, which contains an estimated $3 \times 10^8$ cells, has an extracellular matrix which morphologically and biochemically resembles the extracellular matrix of the adolescent bovine cartilage tissue from which the chondrocytes were obtained.

EXAMPLE 2

$2 \times 10^6$ chrondrocytes are prepared and cultured by the above-described method in a 35 mm culture plate (a density of plated cells of about $2 \times 10^5$ cells/cm²) for 16 days in the presence of $^3$H-proline (10 micro Ci/ml). The scraped cells and medium combined are brought to 25% saturation with ammonium sulfate, and the precipitate is collected by centrifugation following an overnight incubation at 4° C. The pellet is dissolved in 0.5 M acetic acid containing 1 mg/ml type I carrier collagen and 10 micrograms per ml. pepsin. Digestion is carried out for 10 hours at 4° C. The collagen mixture is brought to pH 8 and centrifuged to remove undigested material. The supernatant is again brought to 25% saturation with ammonium sulfate to precipitate the protein. The pellet produced by centrifugation is dissolved in 0.5 M acetic acid and exhaustively dialyzed against the same solution. The collagen, free of labeled, unincorporated amino acid, is lyophilized and subsequently dissolved in 6 M urea with 1% SDS.

The collagen is denatured at 70° C. for 30 hours and electrophoresed under normal and reducing conditions according to Laemli, *Nature*, 227, 680, (1970).

A 5% running gel separates the alpha 1 chains of type II collagen from the alpha 2 chains of type I collagen, and the ratios of labeled alpha 1 to alpha 2 chains is determined. The band containing the alpha 2 chains of the carrier type I collagen contains no label while the band containing alpha 1 chains is highly labeled indicating the production of only collagen type II by the culture.

While the invention has been described according to the best mode presently known to the inventor, modifications obvious to one skilled in the art may be made without departing from the scope of the present invention which is limited only by the following claims.

What is claimed is:

1. A method for culturing chondrocytes to produce cartilage tissue comprising:
    selecting mammalian cartilage tissue providing viable chondrocytes,
    preparing shavings from the cartilage tissue,
    digesting said shavings to remove the extracellular matrix to provide denuded cartilage cells,
    plating said denuded cells in a roller bottle in sufficient density to provide at least a monolayer of cells so that said cells are in surface contact with each other, and
    providing a growth medium and rotating said roller bottle to grow said cells and produce a culture with an extracellular matrix.

2. A method for producing anti-invasion factor comprising the steps of:
    selecing mammalian cartilage tissue providing viable chondrocytes;
    preparing shavings from the cartilage tissue;
    digesting said shavings to remove the extracellular matrix to provide denuded cartilage cells,
    plating said denuded cells in a roller bottle in sufficient density to provide at least a monolayer of cells so that said cells are in surface contact with each other,
    providing a growth medium and rotating said roller bottle to grow said cells and produce a culture with an extracellular matrix, and
    extracting anti-invasion factor from said culture.

3. A method according to claim 1 or claim 2 wherein at least about $2 \times 10^5$ of said denuded cells are plated per cm² surface area of said roller bottle.

4. A method according to claim 2 wherein anti-invasion factor is recovered from the growth medium of said culture.

* * * * *

UNITED STATES PATENT AND TRADEMARK OFFICE
CERTIFICATE OF CORRECTION

PATENT NO. : 4,356,261
DATED : October 26, 1982
INVENTOR(S) : Klaus E. Kuettner

It is certified that error appears in the above—identified patent and that said Letters Patent is hereby corrected as shown below:

On the title page, under References cited, OTHER PUBLICATIONS, the following reference should be listed:

--Jokoby (ed.), Methods in Enzymology, VOL. LVIII, Academic Press, New York, 13, 14, 119-131, 449, 450 (1979)--.

Column 3, line 38, "ther" should read --other--.
Column 3, line 57, "voluem" should read --volume--.

Signed and Sealed this

Nineteenth Day of April 1983

[SEAL]

Attest:

GERALD J. MOSSINGHOFF

Attesting Officer

Commissioner of Patents and Trademarks